(12) United States Patent
Mori et al.

(10) Patent No.: US 6,656,905 B1
(45) Date of Patent: Dec. 2, 2003

(54) CYCLIC TETRAPEPTIDE COMPOUND AND USE THEREOF

(75) Inventors: Hiroaki Mori, Suita (JP); Kazutoshi Sakamoto, Tsuchiura (JP); Yasuhisa Tsurumi, Tsukuba (JP); Shigehiro Takase, Ishioka (JP); Motohiro Hino, Tsuchiura (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/806,500

(22) PCT Filed: Oct. 8, 1999

(86) PCT No.: PCT/JP99/05597

§ 371 (c)(1),
(2), (4) Date: May 4, 2001

(87) PCT Pub. No.: WO00/21979

PCT Pub. Date: Apr. 20, 2000

(30) Foreign Application Priority Data

Oct. 13, 1998 (AU) ............................................. PP6469
Mar. 16, 1999 (AU) ............................................. PP9257

(51) Int. Cl.⁷ ...................... A61K 38/07; A61K 38/12; C07K 5/10; C07K 5/12
(52) U.S. Cl. ............................. 514/11; 514/9; 514/18; 530/317; 530/321; 530/330
(58) Field of Search ................ 530/317, 321, 530/330; 514/9, 11, 18

(56) References Cited

FOREIGN PATENT DOCUMENTS

| GB | 2 309 696 | 8/1997 |
|---|---|---|
| JP | 7-196686 | 8/1995 |
| WO | WO 97/11366 | 3/1997 |
| WO | WO 97/35990 | 10/1997 |
| WO | WO 00/08048 | 2/2000 |

OTHER PUBLICATIONS

Gupta et al., "Characterization of a Phytotoxic Cyclotetrapeptide, a Novel Chlamydocin Analog, from *Verticillium coccosporum*" (1994) Tetrahedron Letters, 35(33), 6009–6012.*

I. Takahashi, et al., The Journal of Antibiotics, vol. 49, No. 5, pp. 453–457, "Selective Inhibition of IL–2 Gene Expression by Trichostatin A, A Potent Inhibitor of Mammalian Histone Deacetylase", May 1996.

* cited by examiner

*Primary Examiner*—Jon P. Weber
(74) *Attorney, Agent, or Firm*—Oblon, Spivak, McClelland, Maier & Neustadt, P.C.

(57) ABSTRACT

A cyclic tetrapeptide compound and use thereof. Especially, a compound WF27082, a process for production of the compound by culturing, in a nutrient medium, a WF27082-producing strain belonging to Acremonium and recovering the compound from a culture broth, a pharmaceutical composition containing the compound as an active ingredient, in association with a pharmaceutically acceptable, substantially non-toxic carrier or excipient, the compound for use as a medicament, a use of the compound for manufacture of a medicament for inhibiting histone deacetylase, a use of the compound for manufacture of a medicament for treating or preventing inflammatory disorders, diabetes, diabetic complications, homozygous thalassemia, fibrosis, cirrhosis, acute promyelocytic leukaemia (APL), protozoal infections, organ transplant rejections, autoimmune diseases, or tumors, a use of histone deacetylase inhibitors as an immunosuppressant or an antitumor agent, and a use of histone deacetylase inhibitors for manufacture of a medicament for treating or preventing organ transplant rejections, autoimmune diseases or tumors are described.

19 Claims, No Drawings

CYCLIC TETRAPEPTIDE COMPOUND AND USE THEREOF

TECHNICAL FIELD

The present invention relates to a cyclic tetrapeptide compound which is useful as a medicament, to a process for producing the same and to a pharmaceutical composition comprising the same.

BACKGROUND ART

Histone deacetylases are known to play an essential role in the transcriptional machinery for regulating gene expression, and histone deacetylase inhibitors induce histone hyperacetylation and affect the gene expression. Therefore, a histone deacetylase inhibitor is useful as a therapeutical or prophylactic agent for several diseases caused by abnormal gene expression, such as inflammatory disorders, diabetes, diabetic complications, homozygous thalassemia, fibrosis, cirrhosis, acute promyelocytic leukaemia (APL), protozoal infection, or the like.

In this connection, a cyclic tetrapeptide compound that can be used as an anti-tumor agent is disclosed in JP-A-7-196686 but this publication is silent on the action against histone deacetylases and the effect against the above-mentioned various diseases.

DISCLOSURE OF INVENTION

The present invention relates to a novel cyclic tetrapeptide compound WF27082 which is useful as a medicament, to a process for producing the same and to a pharmaceutical composition comprising the same.

More particularly, it relates to a cyclic tetrapeptide compound which has a potent inhibitory effect on the activity of histone deacetylase.

The inventors of this invention also found that a histone deacetylase inhibitor, such as the WF27082, has a potent immunosuppressive effect and potent antitumor effect. Therefore, a histone deacetylase inhibitor, such as WF27082, is useful as an active ingredient of an immunosuppressant and an antitumor agent and useful as a therapeutical or prophylactic agent for an organ transplant rejection, autoimmune diseases, tumor, or the like.

Accordingly, one object of this invention is to provide a compound which has biological activities as stated above.

Another object of this invention is to provide a process for the production of WF27082 by fermentation of a WF27082-producing strain belonging to the genus Acremonium in a nutrient medium.

A further object of this invention is to provide a pharmaceutical composition containing, as an active ingredient, the WF27082.

A yet further object of this invention is to provide a use of the histone deacetylase inhibitors, such as WF27082, for treating and preventing diseases stated above.

Thus, the present invention provides the following.
(1) A WF27082 compound of the formula:

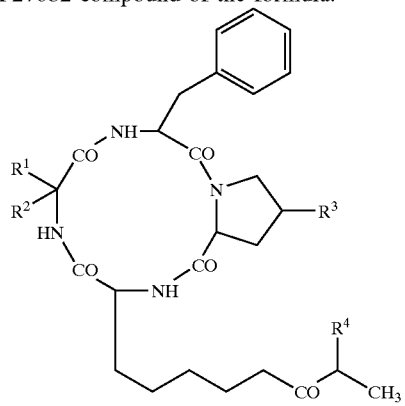

wherein $R^1$ is methyl, R2 is methyl or ethyl, R3 is hydrogen or methyl and $R^4$ is hydroxy optionally having a hydroxy-protective group,
providing that when $R^3$ is hydrogen, $R^2$ is ethyl.
(2) A WF27082 compound of (1) above, wherein $R^1$ is methyl, $R^2$ is ethyl, $R^3$ is methyl and R4 is hydroxy.
(3) A fungal strain belonging to the genus Acremonium, which has a deposit number FERM BP-6539 and which produces a compound having a histone deacetylase inhibitory activity.
(4) A compound having a histone deacetylase inhibitory activity, which is obtained by culturing the fungal stain of (3) above in a nutrient medium and recovering the compound from a culture broth thereof.
(5) A process for producing the WF27082 compound of (1) above, which comprises culturing, in a nutrient medium, a WF27082-producing strain belonging to the genus Acremonium and recovering the compound from a culture broth thereof.
(6) The process of (5) above, wherein the WF27082-producing strain belonging to the genus Acremonium is the fungal strain of (3).
(7) A pharmaceutical composition containing the WF27082 compound of (1) above as an active ingredient, in association with a pharmaceutically acceptable, substantially non-toxic carrier or excipient.
(8) A compound of (1) above for use as a medicament.
(9) A process for producing a compound having a histone deacetylase inhibitory activity, which comprises culturing, in a nutrient medium, a fungal strain belonging to the genus Acremonium, which produces a compound having a histone deacetylase inhibitory activity, and recovering said compound.
(10) A compound having a a histone deacetylase inhibitory activity, which is obtained by culturing, in a nutrient medium, a fungal strain belonging to the genus Acremonium, which produces a compound having histone deacetylase inhibitory activity, and recovering the compound from a culture broth thereof
(11) A histone deacetylase inhibitor comprising a compound of the formula (I):

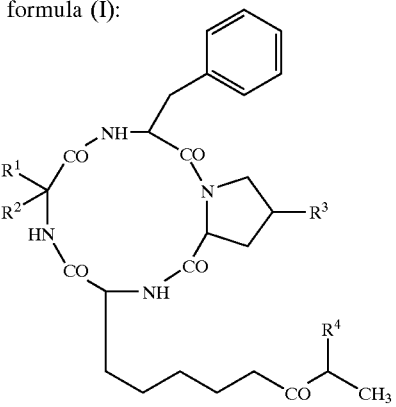

wherein $R^1$ is methyl, $R^2$ is methyl or ethyl, R3 is hydrogen or methyl and $R^4$ is hydroxy optionally having a hydroxy-protective group.

(12) A method for inhibiting histone deacetylase, comprising using a compound (I) used in (11) above.

(13) A use of compound (I) used in (11) above for the manufacture of a medicament for inhibiting histone deacetylase.

(14) A pharmaceutical composition for treating or preventing inflammatory disorders, diabetes, diabetic complications, homozygous thalassemia, fibrosis, cirrhosis, acute promyelocytic leukaemia (APL), organ transplant rejections or autoimmune diseases, which comprises, as an active ingredient, a compound of the formula (1) wherein $R^1$ is methyl, $R^2$ is methyl or ethyl, $R^3$ is hydrogen or methyl and $R^4$ is hydroxy optionally having a hydroxy-protective group.

(15) A method for treating or preventing inflammatory disorders, diabetes, diabetic complications, homozygous thalassemia, fibrosis, cirrhosis, acute promyelocytic leukaemia (APL), or organ transplant rejections, autoimmune diseases, which comprises administering a compound (I) used in (14) above to a human being or an animal.

(16) A use of a compound (I) used in (14) above for the manufacture of a medicament for treating or preventing inflammatory disorders, diabetes, diabetic complications, homozygous thalassemia, fibrosis, cirrhosis, acute promyelocytic leukaemia (APL), organ transplant rejections or autoimmune diseases.

(17) A method for treating or preventing protozoal infections or tumors, which comprises administering a compound WF 27082 used in (1) above to a human being or an animal.

(18) A use of a compound WF27082 used in (1) above for the manufacture of a medicament for treating or preventing protozoal infections or tumors.

(19) A use of a histone deacetylase inhibitor as an immunosuppressant or an antitumor agent.

(20) A use of a histone deacetylase inhibitor for the manufacture of a medicament for treating or preventing organ transplant rejections, autoimmune diseases or tumors.

The compound, which has a potent inhibitory effect on the activity of histone deacetylase, can be represented by the following formula (I):

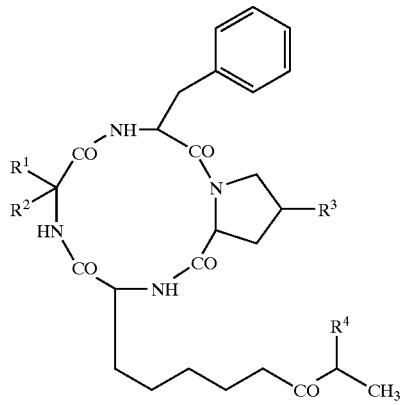

(I)

wherein $R^1$ is methyl, $R^2$ is methyl or ethyl, $R^3$ is hydrogen or methyl and $R^4$ is hydroxy optionally having a hydroxy-protective group.

Of a series of these compounds, particularly the compound of the following formula is a novel compound.

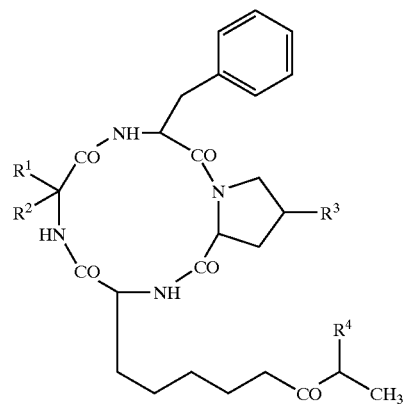

wherein $R^1$ is methyl, $R^2$ is methyl or ethyl, $R^3$ is hydrogen or methyl and $R^4$ is hydroxy optionally having a hydroxy-protective group, providing that when $R^1$ is hydrogen, $R^2$ is ethyl.

The compound of the present invention having the formula (I), wherein $R^1$ is methyl, $R^2$ is methyl or ethyl, R3 is hydrogen or methyl and $R^4$ is hydroxy optionally having a hydroxy-protective group, providing that when R3 is hydrogen, $R^2$ is ethyl, is also referred to as WF27082.

Particulars of the above definitions and the preferred embodiments thereof are explained in detail in the following.

The term "lower" used in the specification is intended to mean 1 to 6 carbon atoms, unless otherwise indicated.

Suitable hydroxy-protective group may include:

1-(lower alkylthio)(lower)alkyl such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$–$C_4$ alkylthiomethyl and the most preferred one may be methylthiomethyl;

trisubstituted silyl such as tri(lower)alkylsilyl (e.g. trimethylsilyl, triethylsilyl, tributylsilyl, tert-butyl-dimethylsilyl, tri-tert-butylsilyl, etc.), lower alkyl-diarylsilyl (e.g. methyl-diphenylsilyl, ethyl-diphenylsilyl, propyl-diphenylsilyl, tert-butyl-diphenylsilyl, etc.), and the like, in which the preferred one may be tri($C_{1-C4}$) alkylsilyl and $C_1$–$C_4$ alkyl-diphenylsilyl, and the most preferred one may be tert-butyl-dimethylsilyl and tert-butyl-diphenylsilyl;

acyl such as aliphatic acyl, aromatic acyl and aliphatic acyl substituted with aromatic group, which are derived from carboxylic and sulfonic acids; and the like.

The aliphatic acyl may include lower alkanoyl which may have one or more suitable substituent(s) such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkyloxy(lower)alkanoyl which may have one or more suitable substituent(s) such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxyheptanoyl, menthyloxyhexanoyl, etc.), camphorsulfonyl, and the like.

The aromatic acyl may include aroyl which may have one or more suitable substituent(s) such as nitro (e.g. benzoyl, toluoyl, xyloyl, naphthoyl, nitrophenyl, dinitrophenyl, nitronaphthoyl, etc.), arenesulfonyl which may have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzensulfonyl, etc.), and the like.

The aliphatic acyl substituted with aromatic group may include ar(lower)alkanoyl which may have one or more suitable substituent(s) such as lower alkoxy and trihalo (lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-tryfluoromethyl-2-propoxy-2-phenylacetyl, etc.), and the like.

When the compound of the above formula (I) has stereoisomers, such isomers are also encompassed in the present invention. The compound of the formula (I) may form a salt, which is also encompassed in the present invention. For example, when a basic group such as an amino group is present in a molecule, an acid addition salt (e.g. salt with an inorganic acid such as hydrochloric acid, hydrobromic acid, sulfuric acid and the like, salt with an organic acid such as methane sulfonic acid, fumaric acid, maleic acid, mandelic acid, citric acid, salicylic acid and the like) is exemplified, and when an acidic group such as carboxyl group is present, a basic salt (e.g. salt with a metal such as sodium, potassium, calcium, magnesium, aluminium and the like, a salt with amino acid such as lysine and the like) is exemplified. In addition, their solvates such as hydrate, ethanolate and the like are also encompassed in the present invention.

In this specification, the following designations of the specific compounds are conveniently used.

| Compound name | $R^1$ | $R^2$ | $R^3$ | $R^4$ |
|---|---|---|---|---|
| WF27082 B | —CH$_3$ | —CH$_2$CH$_3$ | —CH$_3$ | —OH |
| WF27082 E | —CH$_3$ | —CH$_2$CH$_3$ | —H | —OH |
| WF27082 F | —CH$_3$ | —CH$_3$ | —CH$_3$ | —OH |
| FR235220 | —CH$_3$ | —CH$_3$ | —H | —OH |

The WF27082 B has the following physico-chemical properties:

Molecular formula:

$C_{30}H_{44}N_4O_6$

| Molecular weight: | | | |
|---|---|---|---|
| ESI-MS (+): | m/z | 557 (M + H)$^+$ |
| ESI-MS (−): | m/z | 555 (M − H)$^-$ |

Specific rotation: [α]$_D$(23° C.)−129° (c=0.5, in chloroform); Ultraviolet absorption spectrum: λ max (methanol): 235 (sh); λ max (methanol+0.01N HCl): 235 (sh); λ max (methanol+0.01N NaOH): 235 (sh); Solubility: Soluble: methanol, chloroform, ethyl acetate, dimethyl sulfoxide; Insoluble: hexane; Color reaction; Positive: cerium sulfate reaction, iodine vapor reaction, Dragendorff reaction; Negative: ninhydrin reaction, ferric chloride reaction, Molish reaction, Ehrlich reaction; Thin layer chromatography (TLC):

| Stationary phase | Developing solvent | Rf value |
|---|---|---|
| Silica Gel 60 F254* | chloroform:methanol (20:1, v/v) | 0.58 |

*made by E. Merck

High performance liquid chromatography (HPLC): Conditions: Mobile phase: acetonitrile:water=50:50; Column: YMC ODS AM-303 (250 mm L.×4.6 mm I. D.); Flow rate: 1.0 ml/minute; Detection: UV at 210 nm; Retention time: 10.2 minutes;  made by YMC Co., Ltd. Infrared spectrum: ν max (neat): 3300, 2960, 2940, 2880, 1715, 1680, 1660, 1630, 1510, 1440, 1380, 1250, 1060 cm$^{-1}$; $^1$H Nuclear Magnetic Resonance Spectrum: (500 MHz, CDCl$_3$) δ H; 7.52 (1H, d, J=10 Hz, exchangeable), 7.30–7.17 (5H, m), 7.17 (1H, d, J=10 Hz, exchangeable), 5.81 (1H, s, exchangeable), 5.16 (1H, m), 4.67 (1H, m), 4.26–4.16 (2H, m), 4.05 (1H, dd, J=10 & 7.5 Hz), 3.56 (1H, d, J=5 Hz, exchangeable), 3.24 (1H, dd, J=13.5 & 10 Hz), 2.96 (1H, dd, J=13.5 & 6 Hz), 2.73 (1H, dd, J=10 & 8 Hz), 2.62 (1H, m), 2.54–2.29 (4H, m), 2.16 (1H, m), 1.82 (1H, m), 1.66–1.56 (3H, m), 1.38 (3H, d, J=7Hz), 1.41–1.27 (5H, m), 1.28 (3H, s), 0.88 (3H, d, J=6.5 Hz), 0.84 (3H, t, J=7 Hz). $^{13}$C Nuclear magnetic resonance spectrum: (125 MHz, CDCl$_3$) δ C; 212.4 (s), 175.6 (s), 174.1 (s), 173.1 (s), 171.9 (s), 137.0 (s), 129.0 (d)×2, 128.6 (d)×2, 126.7 (d), 72.6 (d), 63.0 (s), 58.0 (d), 54.4 (d), 53.8 (t), 53.3 (d), 37.2 (t), 35.7 (t), 33.0 (t), 32.8 (d), 28.8 (t), 28.8 (t), 27.8 (t), 25.3 (t), 23.2 (t), 22.4 (q), 19.8 (q), 18.1 (q), 8.4 (q). Property of the substance: Neutral substance.

The WF27082 E has the following physico-chemical properties: Molecular formula:

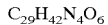
$C_{29}H_{42}N_4O_6$

Molecular weight: ESI-MS (+): m/z 543 (M+H)$^+$; Specific rotation: [α]$_D$(23° C.)−137° (c=0.2, in chloroform); Ultraviolet absorption spectrum: λ max (methanol): 235(sh); λ max (methanol+0.01N HCl): 235(sh); λ max (methanol+0.01N NaOH): 235(sh); Solubility: Soluble: methanol, chloroform, ethyl acetate, dimethyl sulfoxide; Color reaction; Positive: cerium sulfate reaction, iodine vapor reaction, Dragendorff reaction; Negative: ninhydrin reaction, ferric chloride reaction, Molish reaction, Ehrlich reaction; Thin layer chromatography (TLC):

| Stationary phase | Developing solvent | Rf value |
|---|---|---|
| Silica Gel 60 F254* | chloroform:methanol (20:1, v/v) | 0.46 |

*made by E. Merck

High performance liquid chromatography (HPLC): Conditions: Mobile phase: acetonitrile:water=50:50; Column: YMC ODS AM-303* (250 mm L. x 4.6 mm I. D.); Flow rate: 1.0 ml/minute; Detection: UV at 210 nm; Retention time: 7.6 minutes; made by YMC Co., Ltd. Infrared spectrum: ν max (neat): 3300, 2940, 1720, 1690, 1660, 1630, 1530, 1460, 1420, 1380, 1320, 1250, 1150, 1060 cm$^{-1}$; $^1$H Nuclear magnetic resonance spectrum: (500 MHz, CDCl$_3$) δ H; 7.54 (1H, d, J=10 Hz, exchangeable), 7.29–7.17 (5H, m), 7.10 (1H, d, J=10 Hz, exchangeable), 5.82 (1H, s, exchangeable), 5.19 (1H, m), 4.67 (1H, m), 4.26–4.17 (2H, m), 3.85 (1H, m), 3.54 (1H, br.s, exchangeable), 3.30–3.20 (2H, m), 2.96 (1H, dd, J=14 & 6 Hz), 2.54–2.38 (2H, m), 2.36–2.28 (2H, m), 2.18–2.12 (2H, m), 1.84–1.72 (3H, m), 1.67–1.57 (3H, m), 1.38 (3H, d, J=7 Hz), 1.37–1.23 (4H, m), 1.28 (3H, s), 0.83 (3H, t, J=7 Hz); $^{13}$C Nuclear magnetic resonance spectrum: (125 MHz, CDCl$_3$) δ C; 212.4 (s), 175.6 (s), 174.1 (s), 172.8 (s), 171.8 (s), 137.0 (s), 129.0 (d)×2, 128.6 (d)×2, 126.7 (d), 72.6 (d), 63.1 (s), 57.8 (d), 54.4 (d), 53.3 (d), 47.0 (t), 37.3 (t), 35.8 (t), 28.8 (t), 28.7 (t), 27.9 (t), 25.3 (t), 25.0 (t), 24.7 (t), 23.2 (t), 22.4 (q), 19.8 (q). Property of the substance: Neutral substance.

The WF27082 F has the following physico-chemical properties: Molecular formula:

$C_{29}H_{42}N_4O_6$

Molecular weight: ESI-MS (+): m/z 543 (M+H); Specific rotation: $[\alpha]_D(23°$ C.)$-114°$ (c=0.3, in chloroform); Ultraviolet absorption spectrum: λ max (methanol): 235(sh); λ max (methanol+0.01N HCl): 235(sh); λ max (methanol+0.01N NaOH): 235(sh); Solubility: Soluble: methanol, chloroform, ethyl acetate, dimethyl sulfoxide; Color reaction; Positive: cerium sulfate reaction, iodine vapor reaction, Dragendorff reaction; Negative: ninhydrin reaction, ferric chloride reaction, Molish reaction, Ehrlich reaction; Thin layer chromatography (TLC):

| Stationary phase | Developing solvent | Rf value |
|---|---|---|
| Silica Gel 60 F254* | chloroform:methanol (20:1, v/v) | 0.47 |

*made by E. Merck

High performance liquid chromatography (HPLC): Conditions: Mobile phase: acetonitrile:water=50:50; Column: YMC ODS AM-303 (250 mm L.×4.6 mm I. D.); Flow rate: 1.0 ml/minute; Detection: UV at 210 nm; Retention time: 7.6 minutes;  made by YMC Co., Ltd. Infrared spectrum: λ max (neat): 3300, 2930, 1720, 1690, 1660, 1630, 1530, 1440, 1390, 1280, 1180, 1120, 1060 cm$^{-1}$; $^1$H Nuclear magnetic resonance spectrum: (500 MHz, CDCl$_3$) δ H; 7.47 (1H, d, J=10 Hz, exchangeable), 7.30–7.18 (5H, m), 7.17 (1H, d, J=10 Hz, exchangeable), 5.88 (1H, s, exchangeable), 5.14 (1H, m), 4.66 (1H, m), 4.26–4.14 (2H, m), 4.05 (1H, dd, J=10 & 8 Hz), 3.54 (1H, d, J=5 Hz, exchangeable), 3.27 (1H, m) dd, J=14 & 10 Hz), 2.94 (1H, dd, J=14 & 6 Hz), 2.70 (1H, dd, J=10 & 8 Hz), 2.61 (1H, m), 2.53–2.35 (3H, m), 1.80 (1H, m), 1.78 (3H, s), 1.70–1.57 (3H, m), 1.40–1.25 (5H, m), 1.38 (3H, d, J=7 Hz), 1.34 (3H, s), 0.86 (3H, d, J=7 Hz); $^{13}$C Nuclear magnetic resonance spectrum: (125 MHz, CDCl$_3$) δ C; 212.4 (s), 175.6 (s), 174.3 (s), 173.0 (s), 171.9 (s), 137.0 (s), 129.0 (d)×2, 128.6 (d)×2, 126.7 (d), 72.6 (d), 58.8 (s), 57.9 (d), 54.3 (d), 53.9 (t), 53.5 (d), 37.3 (t), 35.7 (t), 33.0 (t), 32.8 (d), 28.8 (t), 28.7 (t), 26.5 (q), 25.2 (t), 23.5 (q), 23.2 (t), 19.8 (q), 18.1 (q). Property of the substance: Neutral substance.

From the above physico-chemical properties and extensive studies, the chemical structures of WF27082 B, E and F were respectively assigned as mentioned above.

The WF27082 can be produced by culturing a WF27082-producing strain belonging to the Acremonium such as Acremonium sp. No.27082 in a nutrient broth and, if necessary, applying chemical modification (e.g. introduction of hydroxy-protective group, etc.).

For example, WF27082 wherein R$^4$ is hydroxy having hydroxy-protective group can be prepared by introducing a hydroxy-protective group into the compound wherein R4 is hydroxy.

Suitable introducing agent of the hydroxy-protective group used in this reaction may be a conventional one such as di(lower)alkyl sulfoxide, for example, lower alkyl methyl sulfoxide (e.g. dimethyl sulfoxide, ethyl methyl sulfoxide, propyl methyl sulfoxide, isopropyl methyl sulfoxide, butyl methyl sulfoxide, isobutyl methyl sulfoxide, hexyl methyl sulfoxide, etc.), trisubstituted silyl compound such as tri (lower)alkylsilyl halide (e.g. trimethylsilyl chloride, triethylsilyl bromide, tributylsilyl chloride, tert-butyl-dimethylsilyl chloride, etc.), lower alkyl-diarylsilyl halide (e.g. methyl-diphenylsilyl chloride, ethyl-diphenylsilyl bromide, propyl-ditolylsilyl chloride, tert-butyl-diphenylsilyl chloride, etc.), and acylating agent which is capable of introducing the acyl group as mentioned before such as carboxylic acid, sulfonic acid and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic trifluoroacetic acid, etc.), aromatic carboxylic acid (e.g. benzoic acid, etc.), a symmetrical acid anhydride, an activated acid amide with a heterocyclic compound contaiining imino function such as imidazole, 4-substituted imidazole, dimethylpyrazole, trazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with an N-hydroxy compound such as N,N-dimethylhydroxylamine, 1-hydroxy-2-(1H)-pyridone, N-hydroxysuccinimide, N-hydroxyphthalmide, 1-hydroxybenzotriazole, 1-hydroxy-6-chlorobenzotriazole, etc.), and the like.

In this reaction, in case where the di(lower)alkyl sulfoxide is used as an introducing agent of the hydroxy-protective group, the reaction is usually conducted in the presence of lower alkanoic anhydride such as acetic anhydride.

Further, in case where the trisubstituted silyl compound is used as an introducing agent of the hydroxy-protective group, the reaction is preferable conducted in the presence of a conventional condensing agent such as imidazole, and the like.

Still further, in case where the acylating agent is used as an introducing agent of the hydroxy-protective group, the reaction is preferably conducted in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal hydrogencarbonate (e.g. sodium hydrogencarbonate, potassium hydrogencarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-N,N-dimethylaminopyridine, etc.), quinoline, and the like.

In case where the acylating agent is used in a free form or its salt in this reaction, the reaction is preferably conducted in the presence of a conventional condensing agent such as a carbodiimide compound [e.g. N,N'-dicyclohexyl-carbodiimide, N-cyclohexyl-N'-(4-diethylaminocyclohexyl) carbodiimide, N,N-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene- N-cyclohexylimine, etc.); an olefinic or acetylenic ether compound (e.g. ethoxyacetylene, β-cyclovinylethyl ether), a sulfonic acid ester of N-hydroxybenzotriazole derivative [e.g. 1-(4-chlorobenzenesulfonyloxy)-6-chloro-1H-benzotriazole, etc.], and the like.

The reaction is usually conducted in a conventional solvent which does not adversely influence the reaction, such as water, acetone, dichloromethane, alcohol (e.g. methanol, ethanol, etc.), tetrahydrofuran, pyridine, N,N-dimethylformamide, etc., or a mixture thereof, and further in case where the base or the introducing agent of the hydroxy-protective group is in liquid, it can also be used as a solvent. The reaction temperature is not critical and the reaction is usually conducted from under cooling to heating.

Characteristics of the Producing Strain No. 27082

The fungal strain No. 27082 was originally isolated from a soil sample, collected in Akita-shi, Akita-ken, Japan. This organism grew very restrictedly on various culture media, and formed orange white to dark brown colonies. The strain produced conidial structures consisting of simple phialidic conidiogenous cells and conidia in slimy heads, while it did not form teleomorph on culture media Its mycological characteristics were as follows.

Cultural characteristics on various agar media are summarized in Table 1. Culture on potato dextrose agar grew very restrictedly, attaining 1.5–2.5 cm in diameter four weeks later at 25° C. This colony surface was centrally raised, cottony, radiately sulcate to wrinkly, exudate, brownish orange to grayish brown, but orange white at the margin. Conidial structures were not observed on the media. The reverse color was dark brown, and brown soluble pigments were produced. Colonies on corn meal agar spread at a similar rate as on potato dextrose agar under the same conditions. The surface was plane, thin, powdery, olive at the center and orange white at the margin. Conidial structures were abundantly formed. The reverse was dark brown at the center and grayish orange to grayish brown at the margin, and pale orange soluble pigments were observed.

The morphological characteristics were determined from the cultures on a Miura's LCA plate (Miura, K. and M. Kudo: Trans. Mycol. Soc. Japan, 11:116–118, 1970). Conidiophores were rarely present, micronematous, short, basitonous, and sometimes verticillate. Conidiogenous cells were discrete, acrogenous, phialidic, and nematogenous to plectonematogenous. They were hyaline, finely roughened, aciculate to subulate, with indistinct collarettes, 21–40 μm long, tapering from (1.5–)2–2.5 μm near the base to 1–2 (–2.5) μm at the tip, and producing conidia in slimy drops. Conidia were hyaline at first, becoming dark olivaceous at maturity, smooth, one-celled, broadly ellipsoidal to ellipsoidal, sometimes pyriform, rounded at the tip, with a small projection at the base, and 3.5–5(–6)×2.5–3(–3.5) μm in size. Vegetative hyphae were hyaline, smooth, septate and branched. The hyphal cells were cylindrical, 2–3 μm in width. Chlamydospores were not observed.

Strain No. 27082 was able to grow in the temperature range of from 2 to 26° C., with the growth optimum at 21 to 22° C. These temperature data were determined on potato dextrose agar (made by NISSUI).

On the basis of the morphological characteristics as compared with fungal taxonomic criteria by von Arx (J. A. von Arx The Genera of Fungi—Sporulating in Pure Culture. 3rd ed., pp.315, J. Cramer, Vaduz, 1974) and Domsch et al. (K. H. Domsch, W. Gams and T. -H. Anderson: Compendium of Soil Fungi. Vol. 1, pp.859, Academic Press, London, 1980), strain No. 27082 was considered to belong to the hyphomycete genus Acremonium Link (1809). Thus, we identified this isolate as one strain of the genus Acremonium, and named it Acremonium sp. No. 27082. The strain has been deposited at the National Institute of Bioscience and Human-Technology, Agency of Industrial Science and Technology, 1–3, Higashi 1-chome, Tsukuba-shi, Ibaraki-ken, 305-8566, Japan, as FERM BP-6539 (deposition date: Oct. 2, 1998).

TABLE 1

Cultural characteristics of strain No. 27082.

| Media | Cultural characteristics |
|---|---|
| Malt extract agar* | G: Very restrictedly, 1.5–2.5 cm<br>S: Circular, plane, felty to cottony, formed some conidial structures, olive brown (4D3-4E3) at the center, orange white (6A2) or grayish orange (6B4-6B5) at the margin<br>R: Brown (7E8) at the center, pale orange (5A3) at the margin |
| Potato dextrose agar (Difco 0013) | G: Very restrictedly, 1.5–2.5 cm<br>S: Circular, centrally raised, cottony, radiately sulcate to wrinkly, exudate, formed no conidial structures, brownish orange (7C4) to grayish brown (7D3), and orange white (6A2) at the margin<br>R: Dark brown (7F7-7F8), and producing brown soluble pigments |
| Czapek's solution agar* | G: Very restrictedly, 1.5–2.5 cm<br>S: Circular to irregular, plane to centrally raised, submerged at the margin, formed no conidial structures, dark brown (7F6) or orange white (6A2) at the center, yellowish white (4A2) at the margin, and brown (6E6-6E8) at the middle<br>R: Dark brown (6F5-6F7), and yellowish white (4A2) at the margin |
| Sabouraud dextrose agar (Difco 0190) | G: Very restrictedly, 1.5–2.0 cm<br>S: Circular, centrally raised, felty, radiately sulcate to wrinkly, formed no conidial structures, grayish orange (6B4-6B5) at the center, and light brown (6D6) to brown (6E6) at the margin<br>R: Brown (7E7) to dark brown (7F7), and producing brown soluble pigments |
| Emerson Yp Ss agar (Difco 0739) | G:Very restrictedly, 1.5–2.5 cm<br>S: Circular, plane, felty, exudate, formed no conidial structures, orange white (5A2), and light brown (6D6- 6D7) at the margin<br>R: Light brown (6D7) to dark brown (6F7) |
| Corn meal agar (Difco 0386) | G: Very restrictedly, 1.5–2.5 cm<br>S: Circular, plane, thin, powdery, formed conidial structures abundantly, olive (3F5-3F6) at the center, and orange white (6A2) at the margin<br>R: Dark brown (7F7) at the center, grayish orange (5B4) to grayish brown (5D3) at the margin, and producing of pale orange soluble pigments |
| MY20 agar* | G: Very restrictedly, 1.5–2.5 cm<br>S: Circular, centrally raised, cottony to floccose, radiately sulcate, formed no conidial structures, and grayish orange (6B4-6B6) at the center, and orange white (5A2) at the margin<br>R: Light brown (6D7-6D8), and light orange (5A5) at the margin |
| Oatmeal agar (Difco 0552) | G: Very restrictedly, 1.5–2.5 cm<br>S: Circular, plane, felty to cottony, radiately sulcate, formed some conidial structures, dull green (30D4-30E4) at the center, orange white (6A2) at the margin, and producing grayish brown soluble pigments |

Abbreviation
G: growth, measuring colony size in diameter,
S: colony surface, R: reverse.
*The compositions of malt extract agar, Czapek's solution agar and MY20 agar are based on JCM Catalogue of Strains (Nakase, T., 6th ed., pp.617, Japan Collection of Microorganisms, the Institute of Physical and Chemical Research, Saitama, 1995).

These characteristics were observed after 28 days of incubation at 25° C. The color descriptions are based on Methuen Handbook of Colour (Kornerup, A. and J. H. Wanscher, 3rd ed., pp.252, Methuen, London, 1978).

It is to be understood that the production of the WF27082 is not limited to the use of the particular organism described herein, which is given for the illustrative purpose only. This invention also includes the use of any mutants which are capable of producing the WF27082 including natural mutants as well as artificial mutants which can be produced from the described organism by conventional means such as recombinant DNA technology, irradiation of X-ray, ultraviolet radiation, treatment with N-methyl-N'-nitro-N-nitrosoguanidine, 2-aminopurine, and the like.

Production of the WF27082

Of the compounds of the above formula (I), the WF27082 is produced when the WF27082-producing strain belonging to the Acremonium is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, sucrose, starch, fructose or glycerin, or the like.

The preferred sources of nitrogen are peanut powder, yeast extract, beef extract, peptone, polypeptone, gluten meal, cotton seed flour, soybean powder, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination, need not be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts, iron salts, or cobalt salts, or the like.

If necessary, especially when the culture medium foams seriously, a defoaming agent, such as liquid paraffin, fatty oil, plant oil, mineral oil, silicone, or the like may be added.

Agitation and aeration of the culture mixture may be accomplished in a variety of ways, such as agitation by a propeller or similar mechanical agitation equipment, by revolving or shaking the fermentor, and the like.

The fermentation is usually conducted at a temperature between about 10° C. and 40° C., preferably 20° C. to 30° C., for a period of about 50 hours to 150 hours, which may be varied according to fermentation conditions and scales.

The resultant culture broth is then subjected for recovery of the WF27082 to various procedures conventionally used for recovery and purification of biological active substances, for instance, solvent extraction with an appropriate solvent or a mixture of some solvents, chromatography or recrystallization from an appropriate solvent or a mixture thereof.

Of the compounds of the formula (I), the compound wherein $R^1$ is methyl, $R^2$ is methyl, R3 is hydrogen and $R^4$ is hydroxy or protected hydroxy (e.g. FR235220) can be prepared, for example, according to the method described in JP-A-7-196686. It can be also obtained by preparing WF27082 as mentioned above and modifying the necessary part. This modification can be performed according to a method known per se.

WF27082 can be in the form of a solvate, which is within the scope of the present invention. The solvate preferably includes a hydrate and an ethanolate.

As examples for showing biological activities of the compounds of the above formula (I), some biological data are shown in the following.

Test 1.

Effect on Lymphocyte Blastogenic Response

WF27082B and FR235220 were used as test compounds.

The lymphocyte blastogenesis test was performed in microtiter plates with each well containing $1 \times 10^5$ splenic cells of Balb/c mice in 0.1 ml RPMI-1640 medium supplemented with 10% fetal bovine serum (FBS), 50 mM 2-mercaptoethanol, penicillin (100 units/ml) and streptomycin (100 $\mu$g/ml), to which anti-CD3 antibody (2C11) (1 $\mu$g/ml) was added. The cells were incubated at 37° C. in a humidified atmosphere of 5% $CO_2$ for 72 hours. After the culture period, suppressive activities of the test samples in lymphocyte blastogenesis were quantified by an MTT [3-(4,5-dimethylthiazol-2-yl)-2,5-diphenyl-2H-tetrazolium bromide (MTT)] dye reduction assay.

WF27082 B was dissolved in methanol and further diluted in RPMI-1640 medium and added to the culture to give final concentrations of 50 ng/ml or less. FR235220 was dissolved in methanol and further diluted in RPMI-1640 medium and added to the culture to give final concentrations of 500 ng/ml or less. The results are shown in Table 2 and Table 3, respectively.

As shown in Tables 2 and 3, WF27082 B and FR235220 suppressed murine lymphocyte blastogenesis induced by anti-CD3 antibody in a dose-dependent manner. WF27082 B was found to have particularly strong effect.

TABLE 2

Effect of WF27082 B on murine lymphocyte blastogenesis induced by anti-CD3 antibody

| Concentration (ng/ml) | 50 | 25 | 12.5 | 6.3 | 3.1 | 1.6 | 0.8 |
|---|---|---|---|---|---|---|---|
| Inhibition (%) | 113.5 | 114.1 | 111.7 | 86.6 | 46.1 | 19.3 | 4.4 |

TABLE 3

Effect of FR235220 on murine lymphocyte blastogenesis induced by anti-CD3 antibody

| Concentration (ng/ml) | 500 | 250 | 125 | 63 | 31 | 16 | 8 | 4 |
|---|---|---|---|---|---|---|---|---|
| Inhibition (%) | 126.0 | 126.0 | 127.2 | 125.3 | 106.0 | 45.1 | −1.3 | −23.4 |

Test 2.

Effect of WF27082 B on DTH (Delayed Type Hypersensitivity Response in Mice

Female Balb/c mice were immunized with sheep red blood cells ($1 \times 10^8$) by subcutaneous injection. WF27082 B was dissolved in 10% a aqueous HCO-60 and administered orally for 8 consecutive days, beginning at one day before the immunization. Six days after the immunization, sheep red blood cells ($1.25 \times 10^8$) were injected into right rear footpad, and 24 hours later, footpad swelling was measured with dial guage (Ozaki MFG Co., Ltd.). The magnitude of the DTH was expressed as the thickness of the challenged right footpad as compared with the untreated left footpad.

As shown in Table 4, the footpad swelling was markedly suppressed by the administration of WF27082 B in a dose-dependent manner without any body weight loss.

TABLE 4

Effect of WF27082 B on DTH response in mice

|  | N | Dose (mg/kg) | Footpad swelling (% Inhibition) | Body weight gain (g) |
|---|---|---|---|---|
| unprimed | 5 |  | 100*** | 1.2 ± 0.2 |
| primed | 10 |  | 0 | 1.2 ± 0.2 |
| WF27082 B | 5 | 10 | 20 | 1.5 ± 0.2 |
|  | 5 | 32 | 34** | 1.5 ± 0.3 |
|  | 5 | 100 | 47*** | 1.1 ± 0.3 |

**P<0.01
***P<0.001

Test 3.
Effect on Activity of Partially Purified Human Histone Deacetylase

The partial purification of human histone deacetylase, the preparation of [$^3$H] acetyl histones, and the assay for histone deacetylase activity were basically performed according to the method as proposed by Yoshida et al. as follows.

Partial Purification of Human Histone Deacetylase—The human histone deacetylase was partially purified from human T cell leukemia Jurkat cells. Jurkat cells (5×10$^8$ cells) were suspended in 40 ml of the HDA buffer consisting of 15 mM potassium phosphate, pH 7.5, 5% glycerol and 0.2 mM EDTA. After homogenization, nuclei were collected by centrifugation (35,000 ×g, 10 min) and homogenized in 20 ml of the same buffer supplemented with 1 M $(NH_4)_2SO_4$. The viscous homogenate was sonicated and clarified by centrifugation (35,000 ×g, 10 min), and the deacetylase was precipitated by raising the concentration of $(NH4)_2SO4$ to 3.5 M. The precipitated protein was dissolved in 10 ml of the HDA buffer and dialyzed against 4 liters of the same buffer. The dialyzate was then loaded onto a DEAE-cellulose (Whatman DE52) column (25×85 mm) equilibrated with the same buffer and eluted with a linear gradient (0–0.6 M) of NaCl (300 ml). A single peak fraction of histone deacetylase activity was eluted between 0.3 and 0.4 M NaCl.

Preparation of [$^3$H] Acetyl Histones—To obtain [$^3$H] acetyl-labeled histones as the substrate for the histone deacetylase assay, 1×10$^8$ cells of Jurkat in 20 ml of RPMI-1640 medium supplemented with 10% FBS, penicillin (50 units/ml) and streptomycin (50 μg/ml) were incubated with 300 MBq [$^3$H] sodium acetate in the presence of 5 μM sodium butyrate for 30 min in 5% $CO_{2-95}$% air atmosphere at 37° C. in a 75 cm2 flask, harvested into a centrifuge tube (50 ml), collected by centrifugation at 1000 rpm for 10 min, and washed once with phosphate-buffered saline. The washed cells were suspended in 15 ml of ice-cold lysis buffer (10 mM Tris-HCl, 50 mM sodium bisulfite, 1% Triton X-100, 10 mM $MgCl_2$, 8.6% sucrose, pH 6.5). After Dounce homogenization (30 stroke), the nuclei were collected by centrifugation at 1000 rpm for 10 min, washed three times with 15 ml of the lysis buffer, and once with 15 ml of ice-old washing buffer (10 mM Tris-HCl, 13 mM EDTA, pH 7.4) successively. The pellet was suspended in 6 ml of ice-cold water using a mixer, and 68 ml of $H_2SO_4$ was added to the suspension to give a concentration of 0.4 N. After incubation at 4° C. for 1 hour, the suspension was centrifuged for 5 min at 15,000 rpm, and the supernatant was taken and mixed with 60 ml of acetone. After overnight incubation at −20° C., the coagulated material was collected by microcentrifugation, air-dried, and stored at −8° C.

Assay for Histone Deacetylase Activity—For the standard assay, 10 μl of [$^3$H]acetyl-labeled histones was added to 90 μl of the enzyme fraction, and the mixture was incubated at 25° C. for 30 min. The reaction was stopped by addition of 10 μl of HCl. The released [$^3$H]acetic acid was extracted with 1 ml of ethyl acetate, and 0.9 ml of the solvent layer was taken into 10 ml of toluene scintillation solution for determination of radioactivity.

As shown in Table 5, WF27082 B, E and F, and FR235220 potently inhibited the activity of partially purified human (Jurkat cells) histone deacetylase in a dose-dependent manner.

TABLE 5

Effect on activity of partially purified human histone deacetylase

| Concentration (ng/ml) |  | 1000 | 100 | 10 | 1 |
|---|---|---|---|---|---|
| Inhibition (%) | WF27082 B | 98.6 | 76.5 | 37.3 | 1.9 |
|  | WF27082 E | 104.9 | 88.5 | 57.6 | 11.1 |
|  | WF27082 F | 91.7 | 74.1 | 36.5 | 11.4 |
|  | FR235220 | 94.6 | 74.6 | 33.7 | −13.1 |

Test 4.
Antitumor Activities of WF27082 B Against Human Tumor Cell Lines

The cytotoxic activity of WF27082 B against human tumor cell lines was determined in vitro as follows. Concentration of the compound required for 50% inhibition of cell growth ($IC_{50}$; ng/ml) was examined by plotting the logarithms of the concentration vs. the growth rate (percentage of control) of the treated cells. Human T cell leukemia Jurkat cells (1×10$^5$ cells/ml) and human colon adenocarcinoma HT-29 cells (5×10$^4$ cells/ml) were treated with WF27082 B in 100 μl of RPMI-1640 medium supplemented with 10% FBS, penicillin (50 units/mil) and streptomycin (50 μg/ml) in 5% $CO_{2-95}$% air atmosphere at 37° C. The cytotoxicity was colorimetrically determined at 550 nm (and 660 nm as a reference) according to the MTT method described above.

The result is shown in Table 6. WF27082 B had potent antitumor activities against Jurkat cells and HT-29 cells.

TABLE 6

Antitumor activities of WF27082 B against human tumor cell lines (in vitro)
IC50 (ng/ml)

| Jurkat | HT-29 |
|---|---|
| 11 | 14 |

The pharmaceutical composition of this invention comprising histone deacetylase inhibitor, such as the compound of the formula (I), is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), protozoal infection or the like. Further, it is useful as an antitumor agent and immunosuppressant, which prevents an organ transplant rejection and autoimmune diseases as exemplified below.

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.; graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; and infections caused by pathogenic microorganisms (e.g. Aspergillus fumigatus, Fusarium oxysporum, Trichophyton asteroides, etc.).

Furthermore, pharmaceutical preparations of the histone deacetylase inhibitor, such as the compound of the formula (I), are useful for the therapy and prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

- autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);
- reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.]
- mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);
- intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migrain, rhinitis and eczema);
- renal diseases (e.g. intestitial nephritis, Goodpasture's syndrome, hemolytic uremic syndrome, and diabetic nephropathy);
- nervous diseases (e.g. multiple myositis, Guilain-Barre syndrome, Meniere's disease, multiple neuritis, solitary neuritis, cerebral infarction, Alzheimer's disease, Parkinson's disease, amyotrophic lateral sclerosis (ALS), and radiculopathy); cerebral ischemic diseases (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), and hypertensive encephalopathy);
- endocrine diseases (e.g. hyperthyroidism, and Basedow's disease);
- hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);
- bone diseases (e.g. osteoporosis);
- respiratory diseases (e.g. sarcoidosis, pulmonary fibrosis, and idiopathic interstitial pneumonia);
- skin diseases (e.g. dermatomyositis, leukoderma vulgaris, ichthyosis vulgaris, photosensitivity, and cutaneous T-cell lymphoma);
- circulatory diseases (e.g. arteriosclerosis, atherosclerosis, aortitis syndrome, polyarteritis nodosa, and myocardosis);
- collagen diseases (e.g. scleroderma, Wegener's granuloma, and Sjögren's syndrome);
- adiposis;
- eosinophilic fasciitis;
- periodontal diseases (e.g. damage to gingiva, periodontium, alveolar bone or substantia ossea dentis);
- nephrotic syndrome (e.g. glomerulonephritis);
- male pattern alopecia, alopecia senile;
- muscular dystrophy;
- pyoderma and Sezary syndrome;
- chromosome abnonmality-associated diseases (e.g. Down's syndrome);
- Addison's disease;
- active oxygen-mediated diseases [e.g. organ injury (e.g. ischenic circulation disorders of organs (e.g. heart, liver, kidney, digestive tract, etc.) associated with preservation, transplantation, or ischemic diseases (e.g. thrombosis, cardial infarction, etc.)):
- intestinal diseases (e.g. endotoxin shock, pseudomembranous colitis, and drug- or radiation-induced colitis):
- renal diseases (e.g. ischemic acute renal insufficiency, chronic renal failure):
- pulmonary diseases (e.g. toxicosis caused by pulmonary oxygen or drugs (e.g. paracort, bleomycin, etc.), lung cancer, and pulmonary emphysema):
- ocular diseases (e.g. cataracta, iron-storage disease (siderosis bulbi), retinitis, pigmentosa, senile plaques, vitreous scarring, corneal alkali burn):
- dermatitis (e.g. erythema multiforme, linear immunoglobulin A bullous dermatitis, cement dermatitis):
- and other diseases (e.g. gingivitis, periodontitis, sepsis, pancreatitis, and diseases caused by environmental pollution (e.g. air pollution), aging, carcinogen, metastasis of carcinoma, and hypobaropathy)];
- diseases caused by histamine release or leukotriene C4 release;
- restenosis of coronary artery following angioplasty and prevention of postsurgical adhesions;
- Autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);
- Human Immunodeficiency Virus (HIV) infection, AIDS;
- allergic conjunctivitis;
- hypertrophic cicatrix and keloid due to trauma, bum, or surgery.

Therefore, the pharmaceutical composition of the present invention is useful for the therapy and prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

The pharmaceutical composition of this invention can be used in the form of pharmaceutical preparation, for example, in a solid, semisolid or liquid form, which contains the histone deacetylase inhibitor, such as the compound of the formula (I), as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in a solid, semisolid, or liquid form, and in addition auxiliary, stabilizing, thickening, solubilizing and coloring agents and perfumes may be used.

For applying the composition to human, it is preferable to apply it by intravenous, intramuscular, topical or oral administration. While the dosage of therapeutically effective amount of the histone deacetylase inhibitor, such as the compound of the formula (I), varies from and also depends upon the age and condition of each individual patient to be treated, when an individual patient is to be treated, in the case of intravenous administration, a daily dose of 0.01–10 mg of the histone deacetylase inhibitor, such as the compound of the formula (I), per kg weight of human being, in the case of intramuscular administration, a daily dose of 0.1–10 mg of the histone deacetylase inhibitor, such as the compound of the formula (1, per kg weight of human being, and in the case of oral administration, a daily dose of 0.5–50 mg of the histone deacetylase inhibitor, such as the compound of the formula (I), per kg weight of human being, is generally given for treatment.

Following examples are given for the purpose of illustrating the present invention in more detail.

EXAMPLE 1

(1) Fermentation Production of WF27082 B

An aqueous seed medium (30 ml) containing 4.0% sucrose, 1.0% glucose, 2.0% soluble starch, 3.0% cotton seed flour, 1.5% soybean flour, 1.0% $KH_2PO_4$, 0.2% $CaCO_3$, 0.05% Adekanol LG-109 (defoaming agent, Asahi Denka Co., Ltd.) and 0.05% Silicone KM-70 (defoaming agent, Shin-Etsu Chemical Co., Ltd.) was poured into a 100-ml Erlenmeyer flask and sterilized at 120° C. for 30 minutes. A loopful of fungus strain No. 27082 was inoculated from a slant culture into the flask and cultured at 25° C. on a rotary shaker at 220 rpm (5.1 cm-throw) for 4 days. The seed culture (6 ml) was inoculated to 20 liters of sterile production medium consisting of 3.0% modified starch, 2.0% cotton seed flour, 0.2% wheat germ, 0.1% $KH_2PO_4$, 0.1% NaCl, 0.0005% $ZnSO_4 \cdot 7H_2O$, 0.05% Adekanol LG-109 and 0.05% Silicone KM-70 (pH 7.0) in a 30-liter jar fermentor. Fermentation was carried out at 25° C. for 4 days under aeration at 20 liters/min and agitation at 200–300 rpm.

(analytical HPLC conditions)

| | |
|---|---|
| column | YMC Pack ODS-AM AM303, S-5 120A (250 mm L. x 4.6 mm I.D., YMC Co., Ltd.) |
| eluent | 50% aqueous acetonitrile |
| flow rate | 1 ml/min. |
| detection | UV at 210 nm |
| retention time | WF27082 B 10.4 min. |

(2) Isolation of WF27082 B

The cultured broth (20L: containing 380 mg of WF27082 B) was extracted with 20L of acetone by intermittent mixing. The acetone extract was filtered with the aid of diatomaceous earth and diluted with the same volume of water. The diluted filtrate was passed through a column (1L) of Diaion HP-20 (Mitsubishi Chemical Co., Ltd.). The column was washed with water and 70% aqueous methanol, and eluted with methanol. The eluate (1L) was diluted with 2L of water and applied on a column (180 ml) of YMC GEL ODS-AM 120-S50 (YMC Co., Ltd.) packed with 45% aqueous acetonitrile. The column was eluted with 45% aqueous acetonitrile and elution was monitored by analytical HPLC indicated above. The portion corresponding to the WF27082 B was concentrated in vacuo to give an aqueous residue. This residue was extracted with ethyl acetate and the extracts were concentrated in vacuo to give an oily residue (containing 351 mg of WF27082 B). The oily residue was dissolved in a small volume of methanol, mixed with 20 ml of silica gel 60 (70–230 mesh, MERCK), and concentrated to dryness. The dry powder was subjected to column chromatography using the same silica gel 60 (230 ml) which was packed with chloroform. The column was eluted with chloroform and elution was monitored by analytical HPLC indicated above. The portion corresponding to the purified WF27082 B was concentrated in vacuo to give 230 mg of a colorless oil.

EXAMPLE 2

(1) Fermentation production of WF27082 E and F

The cultured broth (20L) was obtained in substantially the same manner as in Example 1 (1).

(2) Isolation of WF27082 E and F

The cultured broth (20L) was extracted with 20L of acetone by intermittent mixing. The acetone extract was filtered with the aid of diatomaceous earth and diluted with the same volume of water. The diluted filtrate was passed through a column (1L) of Diaion HP-20 (Mitsubishi Chemical Co., Ltd.). The column was washed with water and 70% aqueous methanol, and eluted with methanol. The eluate (1L) was diluted with 2L of water and applied on a column (180 mL) of YMC GEL ODS-AM 120-S50 (YMC Co., Ltd.) packed with 45% aqueous acetonitrile.

The column was eluted with 45% aqueous acetonitrile and elution was monitored by analytical HPLC indicated below. The portion corresponding to the mixture of WF27082 E and F (500 mL) was diluted with 500 mL of water and applied on a column (180 mL) of YMC GEL ODS-AM 120-S50 (YMC Co., Ltd.) packed with 60% aqueous methanol. The column was eluted with 60% aqueous methanol and the portion corresponding to the mixture of WF27082 E and F was concentrated in vacuo to give an aqueous residue. This residue was extracted with ethyl acetate. and the extracts were concentrated in vacuo to give an oily residue. The oily residue was dissolved in a small volume of methanol and subjected to preparative HPLC, and applied to packed column Fluofix 120E 1EW225 (20mm×250mm, NEOS Co., Ltd.) with 40% aqueous methanol as mobile phase and at flow rate 9.9 ml/min. The portion corresponding to the purified WF27082 E and F (retention: WF27082 E; 74.8 min, WF27082 F; 85.7 min) was concentrated in vacuo to give 8 mg and 18 mg in the form of an oily residue, respectively.

| (analytical HPLC conditions) | |
|---|---|
| column | YMC Pack ODS-AM AM303, S-5 120A (250 mm L. × 4.6 mm I.D., YMC Co., Ltd.) |
| eluent | 40% aqueous acetonitrile |
| temperature | 50° C. |
| flow rate | 1 ml/min. |
| detection | UV at 210 nm |
| retention time | WF27082 E 15.3 min. |
| | WF27082 F 16.1 min. |

This application is based on Application No. 6469/1998 and Application No. 9257/1999 filed in Australia, the content of which is incorporated hereinto by reference.

What is claimed is:

1. A WF27082 compound of the formula:

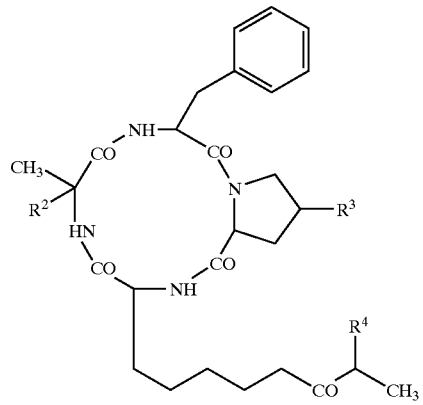

wherein $R^2$ is methyl or ethyl, $R^3$ is hydrogen or methyl and $R^4$ is hydroxy optionally having a hydroxy-protective group, provided that when $R^3$ is hydrogen, $R^2$ is ethyl.

2. A WF27082 compound of claim 1, wherein $R^2$ is ethyl, $R^3$ is methyl and $R^4$ is hydroxy.

3. The compound according to claim 1 obtained by culturing a fungal strain in a nutrient medium and recovering the compound from a culture broth thereof, wherein said strain belongs to the genus Acremonium, has a deposit number FERM BP-6539; and produces the compound according to claim 1.

4. A process for producing the WF27082 compound of claim 1, comprising, culturing a WF27082-producing strain belonging to the genus Acremonium in a nutrient medium and recovering the compound from a culture broth thereof.

5. The process of claim 4, wherein the WF27092-producing strain belonging to the genus Acremonium is the fugal strain which has a deposit number FERM BP-6539 and which produces a compound having a histone deacetylase inhibitory activity.

6. A pharmaceutical composition, comprising the WF27082 compound of claim 1 as an active ingredient and a pharmaceutically acceptable, substantially non-toxic carrier or excipient.

7. A medicament, comprising the WF27082 compound of claim 1 as an active ingredient and an inorganic or organic carrier or excipient.

8. The compound according to claim 1, obtained by chemical synthesis.

9. A method for inhibiting histone deacetylase, comprising contacting the compound according to claim 1 with the histone deacetylase.

10. A method of manufacturing a medicament, comprising contacting the compound according to claim 1 with an organic or inorganic carrier or excipient.

11. A method of making a pharmaceutical composition, comprising contacting the compound according to claim 1 with a pharmaceutically acceptable, substantially non-toxic carrier or excipient.

12. A method for treating a human being or an animal having an inflammatory disorder, diabetes, diabetic complication, homozygous thalassemia, fibrosis, cirrhosis, acute promyelocytic leukaemia (APL), organ transplant rejection, or autoimmune disease, comprising administering a compound according to claim 1.

13. A method of treating a human being or an animal having an inflammatory disorder, diabetes, diabetic complication, homozygous thalassemia, fibrosis, cirrhosis, acute promyelocytic leukaemia (APL), organ transplant rejection or autoimmune disease, comprising administering a medicament comprising a compound according to claim 1 to the human being or animal.

14. A method for treating a human being or animal having a protozoal infection or tumor, comprising administering the compound of claim 1 to the human being or animal.

15. A method for treating a human being or animal having a protozoal infection or tumor, comprising administrating the medicament comprising the compound according to claim 1 to the human being or animal.

16. A method of treating a human being or animal having a protozoal infection, tumor, inflammatory disorder, diabetes, diabetic complication, homozygous thalassemia, fibrosis, cirrhosis, acute promyelocytic leukaemia (APL), organ transplant rejection or autoimmune disease, comprising administering a pharmaceutical composition comprising a compound according to claim 1. to the human being or animal.

17. A method of treating a human being or animal having or suffering from a organ transplant rejection, autoimmune disease or tumor, comprising administering a medicament comprising a compound according to claim 1 to the human being or animal.

18. An isolated WF27082 compound of the formula:

wherein $R^2$ is methyl or ethyl, $R^3$ is hydrogen or methyl and $R^4$ is hydroxy optionally having a hydroxy-protective group, provided that when $R^3$ is hydrogen, $R^2$ is ethyl.

19. A pure WF27082 compound of the formula:

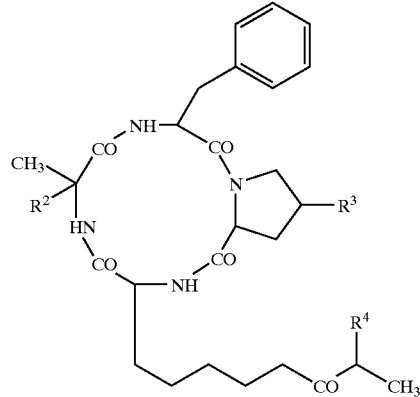

wherein $R^2$ is methyl or ethyl, $R^3$ is hydrogen or methyl and $R^4$ is hydroxy optionally having a hydroxy-protective group, provided that when $R^3$ is hydrogen, $R^2$ is ethyl.

* * * * *